(12) United States Patent
Hayes

(10) Patent No.: US 6,247,177 B1
(45) Date of Patent: Jun. 19, 2001

(54) EYEGLASSES-HELD SUN VISOR

(76) Inventor: Ashley Marrell Hayes, 2103 Sunset Pl. Suite 203, Nashville, TN (US) 37212

( * ) Notice: Subject to any disclaimer, the term of this patent is extended or adjusted under 35 U.S.C. 154(b) by 0 days.

(21) Appl. No.: 09/658,524

(22) Filed: Sep. 9, 2000

Related U.S. Application Data

(60) Provisional application No. 60/153,536, filed on Sep. 13, 1999.

(51) Int. Cl.[7] .................................................. A61F 9/00
(52) U.S. Cl. ................................. 2/12; 2/209.13; 351/155
(58) Field of Search .................................. 2/12, 15, 171, 2/171.04, 209.13, 209.12, 175.1, 195.1; 351/155

(56) References Cited

U.S. PATENT DOCUMENTS

| | | | |
|---|---|---|---|
| 947,636 | * | 1/1910 | Degges ........................................ 2/12 |
| 4,179,753 | * | 12/1979 | Aronberg et al. ........................ 2/10 |
| 4,277,847 | * | 7/1981 | Florio ........................................ 2/12 |
| 4,543,667 | * | 10/1985 | Garbutt ..................................... 2/13 |
| 4,606,453 | * | 8/1986 | Burns ....................................... 206/5 |
| 4,768,231 | * | 9/1988 | Schrack .................................... 2/12 |
| 5,473,778 | * | 12/1995 | Bell .......................................... 2/10 |
| 5,894,604 | * | 4/1999 | Crabb et al. ........................ 2/209.13 |

* cited by examiner

Primary Examiner—John J. Calvert
Assistant Examiner—Katherine Moran

(57) ABSTRACT

An eyeglasses-held sun visor to provide sunshade to the face of the person. The eyeglasses-held sun visor comprises a visor, a headband, two pieces of flat, elasticized material, and four openings, two on the inside portion of the headband through which the arms of a pair of eyeglasses would be inserted, and one at each end of the headband through which the arms of said eyeglasses would exit, thereby securing said eyeglasses-held sun visor. The openings, along with the elastic nature of the material the eyeglasses slide under, secure the sun visor to the eyeglasses of a person thereby eliminating the necessity for any other apparatus to secure said sun visor to the head of the person.

1 Claim, 1 Drawing Sheet

EYEGLASSES-HELD SUN VISOR

CROSS-REFERENCE TO RELATED APPLICATIONS

This application claims benefit of U.S. Provisional Patent Application No. 60/153,536 filed Sep. 13, 1999 by the instant applicant, Ashley M. Hayes.

STATEMENT REGARDING FEDERALLY SPONSORED RESEARCH OR DEVELOPMENT

Not applicable

REFERENCE TO A MICROFICHE APPENDIX

Not applicable

BACKGROUND OF THE INVENTION

1. Field of the Invention

The instant invention relates generally to sun visors, and more specifically it relates to a sun visor that will attach to a person's eyeglasses via insertion through two pieces of flat, elasticized material located on either side of the interior of the headband (openings A and B, left and right, respectively) of the sun visor, spaced equally on the inside portion of the headband of the visor, with an opening at each end of the elasticized material, between the elasticized material and the headband to which it is attached (openings C and D, left and right, respectively), whereby the left arm of the eyeglasses would enter through opening A and exit through opening C, and the right arm of the eyeglasses would enter through opening B and exit through opening D.

2. Description of the Prior Art

Numerous sun visors have been provided in prior art that are adapted to attach to a pair of eyeglasses which include U.S. Pat. No. D341,695 to Vandiver; U.S. Pat. No. D320,609 to Cross, et al.; U.S. Pat. No. 5,438,378 to Blatter; U.S. Pat. No. 4,543,667 to Garbutt; and U.S. Pat. No. 5,712,697 issued Jan. 27, 1998 to Walton, yet these visors had some noteworthy drawbacks. One of the drawbacks of the aforementioned patented sun visors is that they do not provide protection for the entire face. These inventions leave the forehead and the temples of the wearer exposed to sunlight, among other things. Latter U.S. Pat. No. 5,553,321, issued Sep. 10, 1996 to Cassel, improved upon some of the drawbacks by providing a design which curved around the wearer's head more, but it still suffers the disadvantage of not having a headband to both protect the wearer's forehead from sunlight and to absorb perspiration from the forehead of the wearer. U.S. Pat. No. 5,553,321 also suffers the disadvantage of being created for wearers of only "conventional" eyeglasses.

OBJECTS AND SUMMARY OF THE INVENTION

Accordingly, it is an object of the invention to provide an improved visor which attaches to most any pair of eyeglasses, not just those of conventional design.

It is another object of the invention to provide an improved visor, which is simple in construction, economic to produce, versatile, lightweight, easily portable, rugged and washable.

It is another object of the invention to provide an improved visor, which provides sunshade to the forehead of the wearer, as well as to the rest of the face.

It is a further object of the invention to provide an improved visor, which provides sunshade to the temples of the wearer, preventing sunlight from entering the eyes of the wearer from either side of the face.

It is a still further object of the invention to provide an improved visor which is sleek in design, and which will provide sunshade to the face of the wearer by attaching to his/her eyeglasses.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

DETAILED DESCRIPTION OF THE INVENTION

Figure 1:
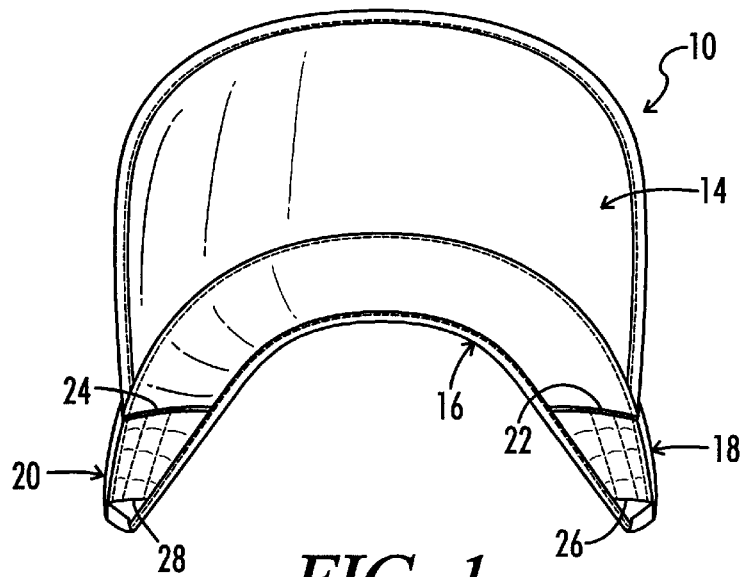
FIG. 1 is a bottom view of the eyeglasses-held sun visor which attaches to eyeglasses or sunglasses.
Figure 2:
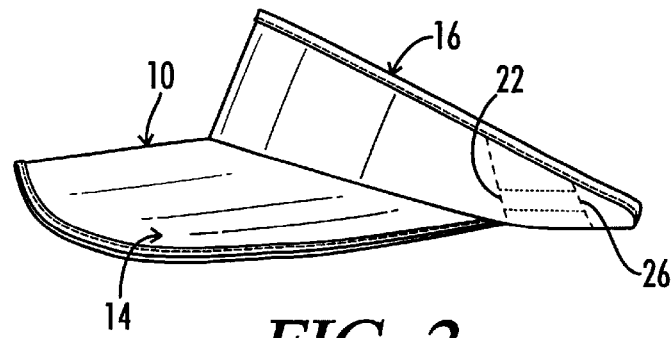
FIG. 2 is a side view of the eyeglasses-held sun visor of FIG. 1.
Figure 3:
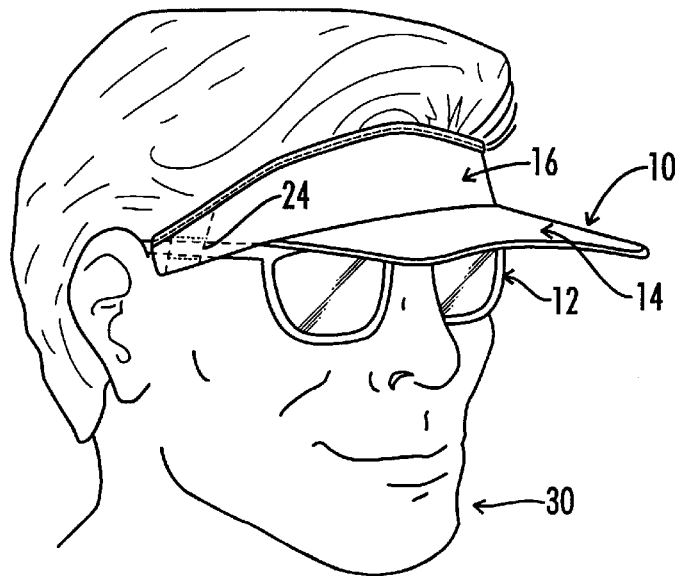
FIG. 3 is a perspective view of the person wearing the instant invention.

Turning now descriptively to the drawings, in which similar reference characters denote similar elements throughout the several views, FIGS. 1 through 3 illustrate an eyeglasses-held sun visor 10 which attaches to eyeglasses 12. The eyeglasses-held sun visor 10 consists of a visor 14 with a headband 16, two pieces of flat, elasticized material 18, 20 sewn onto the headband 16 of the visor 14, one on the left side and one on the right, approximately one inch from each end of the headband 16, and being the same vertical length as the headband, underneath which the arms of the eyeglasses 12 can be inserted via openings 22, 24 between the elastic pieces of material 18, 20 and the headband 16 to which they are sewn. These openings, or places of insertion 22, 24, are on the side of the elasticized material nearest the interior of the headband 16, and openings, or places of exit 26, 28 are at the upper, outermost corner of each flat piece of elasticized material, nearest the exterior of the headband 16, where the stitching of the elasticized material to the headband 16 has ceased, through which the arms of the eyeglasses 12 can exit.

The visor 14 can be fabricated out of a cloth, or soft pliable material, with a cardboard stiffness therein to provide sunshade over the person 30. The headband 16 is attached to the visor 14 and can be fabricated out of the same cloth used for said visor 14, and aids in providing sunshade to the forehead of the person 30, in addition to absorbing perspiration from the forehead of the person 30.

The front openings 22, 24 between the flat, elasticized material 18, 20 and interior of the headband 16 of the eyeglasses-held sun visor 10 will be underneath the part of the elasticized material 18, 20 which is closest to the interior of the headband 16, said elasticized material 18, 20 being sewn to the headband 16 with two rows of angled stitching extending from the innermost portion of the elasticized material 18, 20, to the outermost portion of the elasticized material 18, 20, creating a place of entry 22, 24 for the arms of the eyeglasses 12, as well as a place of exit 26, 28 so as to enable the eyeglasses-held sun visor 10 to attach to the eyeglasses 12 in a balanced and secure manner.

Operation of the Invention

To use the eyeglasses-held sun visor 10 shown in FIGS. 1 through 3, the person 30 first turns the eyeglasses-held sun visor 10 upside-down with the visor 14 facing his or her body and inserts the arms of his or her eyeglasses 12 through the front openings 22, 24 between the elasticized material 18, 20 and the interior portion of the headband 16, the left arm of the eyeglasses 12 entering through the left front opening 22, the right arm of the eyeglasses 12 entering through the right front opening 24, and continues to push the arms of the eyeglasses 12 through the openings 22, 24 until the arms of the eyeglasses 12 exit through the rear openings 26, 28 (left and right, respectively) at the ends of the headband 16 portion of the eyeglasses-held sun visor 10. The openings 22, 24, 26, 28 provide the only necessary method of attachment to firmly secure the eyeglasses-held sun visor 10 to the eyeglasses 12 of the person 30.

List of Reference Numbers

10 eyeglasses-held visor
12 eyeglasses
14 visor
16 headband
18 left elasticized material
20 right elasticized material
22 left front opening
24 right front opening
26 left rear opening
28 right rear opening
30 person It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What I claim as my invention is new and desired to be protected by Letters Patent is set forth in the appended claim:

1. An eyeglasses-held sun visor which comprises: a visor to provide sunshade over the eyes of the person; a headband to provide sunshade to and absorb perspiration from the forehead of the person; two flat pieces of elasticized material which are the same vertical length as the headband, and approximately one to one-and-a-half inches wide, sewn onto the inside of each end the headband portion of the visor, in such a way as to provide an opening at the innermost portion of each piece of elasticized material, and an opening at the outermost portion of each piece of elasticized material.

\* \* \* \* \*